(12) United States Patent
Kao et al.

(10) Patent No.: US 6,303,777 B1
(45) Date of Patent: Oct. 16, 2001

(54) PROCESS FOR OBTAINING HIGHLY ESTERIFIED POLYOL FATTY ACID POLYESTERS HAVING REDUCED LEVELS OF DIFATTY KETONES AND β-KETOESTERS

(75) Inventors: Ju-Nan Kao, Cincinnati; John Keeney Howie, Oregonia; Patrick Joseph Corrigan; Richard Gerard Schafermeyer, both of Cincinnati; Katherine Eleanor Flynn; Nelson James Holzschuh, both of Fairfield; David Joseph Bruno, Jr., Hamilton, all of OH (US)

(73) Assignee: The Procter & Gamble Co., Cincinnati, OH (US)

(*) Notice: Subject to any disclaimer, the term of this patent is extended or adjusted under 35 U.S.C. 154(b) by 0 days.

(21) Appl. No.: 08/271,273

(22) Filed: Jul. 6, 1994

Related U.S. Application Data

(63) Continuation of application No. 07/957,468, filed on Sep. 16, 1992, now abandoned, which is a continuation of application No. 07/724,611, filed on Jul. 2, 1991, now abandoned, which is a continuation-in-part of application No. 07/580,706, filed on Sep. 11, 1990, now abandoned.

(51) Int. Cl.$^7$ .......................... C07H 13/02; C07H 11/00; C07H 1/00; C07H 1/06
(52) U.S. Cl. .................. 536/119; 536/115; 536/116; 536/124; 536/127
(58) Field of Search .................. 536/119, 115, 536/116, 124, 127

(56) References Cited

U.S. PATENT DOCUMENTS

| | | | |
|---|---|---|---|
| 3,714,144 | 1/1973 | Fuege | 260/234 |
| 3,792,041 | 2/1974 | Yamagishi et al. | 260/234 |
| 3,963,699 | 6/1976 | Rizzi et al. | 536/119 |
| 4,298,730 | 11/1981 | Galleymore | 536/119 |
| 4,334,061 * | 6/1982 | Bossier, III | 536/119 |
| 4,517,360 | 5/1985 | Volpenhein | 536/119 |
| 4,518,772 * | 5/1985 | Volpenhein | 536/119 |
| 4,611,055 | 9/1986 | Yamaoto | 536/119 |
| 4,778,881 | 10/1988 | Nieuwenhuis et al. | 523/119 |
| 4,931,552 | 6/1990 | Gibson et al. | 536/119 |
| 4,973,682 * | 11/1990 | Willemse | 536/124 |
| 5,043,438 | 8/1991 | Buter | 536/115 |
| 5,135,573 | 8/1992 | van den Berg et al. | 75/739 |

FOREIGN PATENT DOCUMENTS

| | | |
|---|---|---|
| 27592/88 | 12/1987 | (AU) . |
| 49746/90 | 2/1990 | (AU) . |
| 25 03 195 | 7/1976 | (DE) . |
| 254376 | 1/1988 | (EP) . |
| 256585 | 2/1988 | (EP) . |
| 320043 | 6/1988 | (EP) . |
| 301634 | 2/1989 | (EP) . |
| 315265 | 5/1989 | (EP) . |
| 319091 | 6/1989 | (EP) . |
| 322971 | 7/1989 | (EP) . |
| 323670 | 7/1989 | (EP) . |
| 349059 | 1/1990 | (EP) . |
| 383404 | 8/1990 | (EP) . |
| 1250204 | 10/1971 | (GB) . |
| 50-135016 | 10/1975 | (JP) . |

OTHER PUBLICATIONS

Rizzi & Taylor, "A Solvent–Free Synthesis of Sucrose Polyesters", *Journal of the American Oil Chemists Society*, vol. 55, pp. 398–401 (1978).

Felder et al. "Elementary Principles of Chemical Process", p. 82 (Wylie, 1978).

McCabe and Smith, "Unit Operations of Chemical Engineering", 3d Ed., p. 66 (McGraw–Hill, 1976).

Levenspiel, "Chemical Reaction Engineering", pp. 97–98, Wiley & Sons, 1972.

Fuege et al., "Preparation of Sucrose Esters by Interesterification", *Journal of the American Oil Chemists Society*, vol. 47, pp. 56–60 (1970).

Vol. 1, p. 31 of Procter & Gamble's Food Additive Petition, submitted to the Food & Drug Administration in Apr., 1986.

\* cited by examiner

*Primary Examiner*—Gary Geist
*Assistant Examiner*—Everett White
(74) *Attorney, Agent, or Firm*—Erich D. Hemm; Carl J. Roof

(57) ABSTRACT

An improved, solvent-free, two-stage transesterification process for preparing, from a polyol and fatty acid esters of an easily removable alcohol highly esterified polyol fatty acid polyesters having reduced levels of difatty ketones and β-ketoesters is disclosed. These reduced levels of difatty ketones/β-ketoesters are achieved by controlling the level of generated alcohol in the liquid phase of the reaction mixture and heating the reaction mixture to certain temperatures during the second stage of this improved process. Other optional reaction conditions, such as keeping the molar ratio of fatty acid esters to polyol within a specified range and reducing the level of basic catalyst, can also be used during the second stage reaction to further reduce the level of difatty ketones and/or β-ketoesters.

18 Claims, No Drawings

PROCESS FOR OBTAINING HIGHLY ESTERIFIED POLYOL FATTY ACID POLYESTERS HAVING REDUCED LEVELS OF DIFATTY KETONES AND β-KETOESTERS

CROSS REFERENCE TO RELATED APPLICATIONS

This is a continuation of copending application Ser. No. 07/957,468, filed on Sep. 16, 1992, now abandoned which is a continuation of U.S. Ser. No. 07/724,611 filed Jul. 2, 1991, now abandoned, which is a continuation in part of U.S. Ser. No. 07/580,706 filed Sep. 11, 1990, now abandoned.

TECHNICAL FIELD

This application relates to the synthesis of highly esterified polyol fatty acid polyesters, especially highly esterified sucrose polyesters. This application particularly relates to an improved, solvent-free, two-stage trans-esterification process for preparing such polyesters having reduced levels of difatty ketones and β-ketoesters.

A number of different processes have been disclosed in the art for preparing highly esterified polyol fatty acid polyesters, in particular sucrose polyesters useful as reduced calorie fat substitutes. One such process for preparing these polyesters involves a solvent-free, essentially two-step transesterification of the polyol (e.g., sucrose) with the fatty acid esters of an easily removable alcohol (e.g., fatty acid methyl esters). In the first step, a mixture of sucrose, methyl esters, alkali metal fatty acid soap and a basic esterification catalyst are heated to form a melt. The amount of methyl esters is such that the melt forms primarily partial fatty acid esters of sucrose, e.g., sucrose mono-, di- and/or triesters. In the second step, an excess of methyl esters are added to this melt which is then heated to convert the partial sucrose esters to more highly esterified sucrose polyesters, e.g., sucrose hexa-, hepta-, and particularly octaesters. See, for example, U.S. Pat. No. 3,963,699 (Rizzi et al), issued Jun. 15, 1976; U.S. Pat. No. 4,517,360 (Volpenhein), issued May 14, 1985; and U.S. Pat. No. 4,518,772 (Volpenhein), issued May 21, 1985, which disclose solvent-free, two-step trans-esterification processes for preparing highly esterified polyol fatty acid polyesters, in particular highly esterified sucrose polyesters.

In some processes for preparing highly esterified polyol fatty acid polyesters, all of the fatty acid methyl esters are added to the polyol (e.g., sucrose) at the beginning of the reaction, i.e. a one-step addition process. See, for example, U.S. Pat. No. 4,611,055 (Yamamoto et al), issued Sep. 9, 1986. Like the previously described two-step processes, such one-step processes first form primarily partial fatty acid esters of sucrose that are then converted to more highly esterified sucrose polyesters. Accordingly, these single-step and two-step processes are collectively referred to hereafter as "two-stage" transesterifications, wherein the "first stage" involves the formation of the partial esters and wherein the "second stage" involves the conversion of the partial esters to more highly esterified polyesters.

In addition to highly esterified sucrose polyesters, this two-stage transesterification reaction typically forms by-products. One such by-product formed is difatty ketones. It is believed these difatty ketones result from β-ketoesters formed primarily during the second stage of the transesterification reaction; β-ketoesters can also form, to a more limited extent, during the first stage of the transesterification reaction.

These β-ketoesters are formed as a result of a Claisen condensation. In this Claisen condensation, two equivalents of the fatty acid methyl esters are condensed in the presence of one equivalent of a base. (A similar Claisen condensation can occur involving one or more sucrose esters.) In the first step of this condensation, a proton from the α-carbon atom on the methyl ester is removed by the base to give the resulting methyl ester anion and methanol. In the second step of this condensation, there is a nucleophilic attack by this methyl ester anion on the carbonyl of another fatty acid methyl ester with the concomitant loss of methoxide to give the β-ketoester. This β-ketoester may then lose carbon dioxide (decarboxylation) by either a hydrolytic or thermalytic pathway to yield the difatty ketones.

From the standpoint of sucrose polyester purity, it would be desirable to reduce the level of difatty ketones and/or β-ketoesters that are formed. However, this reduction in difatty ketone/β-ketoester formation needs to be carried out in a manner such that the yield of highly esterified sucrose polyesters, particularly sucrose octaesters, is not decreased significantly.

BACKGROUND ART

U.S. Pat. No. 3,963,699 (Rizzi et al), issued Jun. 15, 1976, discloses the preparation of polyol polyesters (in particular sucrose polyesters), by a solvent-free, two-stage transesterification of the polyol (e.g., sucrose) with fatty acid lower alkyl esters (e.g., fatty acid methyl esters) by: (1) heating (preferably to from about 130° to 145° C. under a pressure of from about 0.5 mm to about 25 mm Hg.) a mixture of sucrose, methyl esters, alkali metal fatty acid soap and a basic catalyst to form a melt; and (2) adding to this melt excess methyl esters to provide the sucrose polyesters.

U.S. Pat. No. 4,517,360 (Volpenhein), issued May 14, 1985, discloses the preparation of polyol polyesters, in particular sucrose polyesters, by a solvent-free, two-stage trans-esterification of the polyol (e.g., sucrose) with fatty acid lower alkyl esters (e.g., fatty acid methyl esters) by: (1) heating (preferably to from about 130° to 145° C. under a pressure of from about 0.5 mm to about 25 mm Hg.) a mixture of sucrose, methyl esters, alkali metal fatty acid soap, and a potassium, sodium or barium carbonate catalyst to form a melt; and (2) adding to this melt excess methyl esters to provide the sucrose polyesters.

U.S. Pat. No. 4,518,772 (VolDenhein), issued May 21, 1985, discloses the preparation of polyol polyesters, in particular sucrose polyesters, by a solvent-free, two-stage transesterification of the polyol (e.g., sucrose) with fatty acid lower alkyl esters (e.g., fatty acid methyl esters) by: (1) heating (preferably to from about 130° to 145° C. under a pressure of from about 0.5 mm to about 25 mm Hg.) a mixture of sucrose, methyl esters, alkali metal fatty acid soap, and basic catalyst where the soap:sucrose molar ratio is from about 0.6:1 to about 1:1 to form a melt; and (2) adding to this melt excess methyl esters to provide the sucrose polyesters.

European patent application 256,585 (van der Plank et al), published Feb. 24, 1988, alleges that the catalysts used in the process of U.S. Pat. No. 3,963,699, and the way in which these catalysts are used, increases the risk of forming by-products, e.g., by ester condensation, leading to the formation of β-ketoesters, e.g., by the reducing effect of sodium hydride, the recommended catalyst in the process of this U.S. patent. See page 2, lines 37–39. By-product formation is allegedly minimized by using a different process, e.g., forming an alkaline solution of sucrose which is then added to a mixture of soap and fatty acid methyl esters, followed by removal of the water and then heating to 110°–140° C. to form the sucrose polyesters.

European patent application 322,971 (Willemse), published Jul. 5, 1989, discloses a two-stage process for the transesterification of a polyol (e.g., sucrose) with fatty acid lower alkyl esters (e.g., fatty acid methyl esters) to provide polyol polyesters (e.g., sucrose polyesters). Pressure control is used during the first stage trans-esterification so that the sucrose is converted primarily to the corresponding monoesters and/or oligoesters, leading to higher yields of sucrose polyesters during the second stage transesterification. See page 2, right-hand column, lines 33–37. Pressure conditions used are from 60 to 180 millibars, preferably from 90 to 150 millibars. See page 3, left-hand column, lines 53–58. Pressure control during the first stage is also alleged to reduce foam formation. See page 2, right-hand column, lines 40–43. During the second stage, the pressure is reduced to less than 25 millibars, most preferably less than 5 millibars. See page 3, right-hand column, lines 15–23.

European patent application 349,059 (Willemse), published Jan. 3, 1990, discloses a process for making polyol polyesters (e.g., sucrose polyesters) in which a polyol and/or fatty acid oligoester thereof, is esterified by reaction with fatty acid lower alkyl esters (e.g., fatty acid methyl esters) in the presence of a transesterification catalyst and, optionally, an emulsifier. A stripping agent is used at least during the second stage of the transesterification to accelerate the removal of generated alcohol, e.g., methanol, to achieve high degrees (e.g., above 85%) of conversion to sucrose polyesters. See page 2, lines 46–54. Suitable stripping agents include inert gases, such as nitrogen, and volatile inert organic compounds, preferably hexane or short chain alkyl methyl esters. See page 3, lines 2–4 and 20–21.

European Datent application 323,670 (Meszaros et al). published Jul. 12, 1989, discloses a process for making polyol polyesters (e.g., sucrose polyesters) involving a two-stage transesterification of the polyol (e.g., sucrose) with a fatty acid lower alkyl ester (e.g., fatty acid methyl esters). The soap level is reduced after the reaction has reached a degree of conversion of from 15 to 60% to avoid undesired higher viscosities in the reaction mixture due to soap separation during the later stages of the reaction. See page 2, right-hand column, lines 18–23, and 27–43. This reduction in soap level can be carried out by a variety of methods, including filtration. See paragraph bridging pages 2 and 3.

U.S. Pat. No. 4,931,552 (Gibson et al), filed Jun. 14, 1989, issued Jun. 5, 1990, discloses the production of polyol polyesters (e.g. sucrose polyesters) having good color by reacting the polyol (e.g., sucrose) with lower alkyl esters of fatty acids (e.g., fatty acid methyl esters) having a "carbonyl content" or "carbonyl value" of less than about 200 ppm on a carbonyl group basis. See Column 2, lines 17–22. These "carbonyls" include unspecified ketones. See Column 2, lines 45–47. It is indicated that a special advantage of the lower carbonyl content of the lower alkyl esters of the fatty acid is that the level of esterification catalyst can be reduced to less than about 0.1, preferably to less than about 0.05, more preferably to less than about 0.01, molar equivalents of catalyst per mole of polyol. It is also stated that this low level of catalyst results in improved color as compared to conventional catalyst levels. See Column 7, lines 10–16.

DISCLOSURE OF THE INVENTION

The present invention relates to an improved solvent-free, two-stage transesterification process for preparing highly esterified polyol fatty acid polyesters, in particular highly esterified sucrose polyesters, from a polyol and fatty acid esters of an easily removable alcohol. The first stage of this process comprises forming polyol fatty acid partial esters from a reaction mixture containing a polyol having more than 4 esterifiable hydroxy groups and at least a portion of the fatty acid esters of the easily removable alcohol in the presence of an effective amount of a basic catalyst, and optionally an effective amount of a soap emulsifier. The second stage of this process comprises forming highly esterified polyol fatty acid polyesters (e.g., sucrose polyesters) from a reaction mixture containing the polyol fatty acid partial esters, the remaining portion of the fatty acid esters and an effective amount of a basic catalyst.

The improvement in this two-stage transesterification process according to the present invention involves carrying out the second stage under reaction conditions that provide a combined level of difatty ketones and β-ketoesters of about 300 ppm or less in the resulting highly esterified polyol fatty acid polyesters, after any residual fatty acid esters, basic catalyst and soap emulsifier having been removed. These reaction conditions involve a combination of at least the following:

(a) controlling the level of easily removable alcohol in the liquid phase of the second stage reaction mixture to from about 10 to about 150 ppm; and (b) heating the second stage reaction mixture to temperatures in the range of from about 175° to about 275° F. (from about 79.4° to about 135° C.).

In addition to the combination of reaction conditions (a) and (b), above, one or more of the following optional reaction conditions can also be used in the improved process of the present invention to further reduce the level of difatty ketones and/or β-ketoesters;

(c) keeping the molar ratio of fatty acid esters of the easily removable alcohol, to each esterifiable hydroxy group of the polyol in the second stage reaction mixture, in the range of from about 0.9:1 to about 1.4:1;

(d) removing materials having particle sizes greater than about 1 micron when the transesterification reaction reaches from about 50 to about 75% of completion;

(e) when alkali metal alkoxides of lower alcohols are used as the basic catalyst, using the form that has been prepared and remains dissolved in the respective lower alcohol;

(f) reducing the level of basic catalyst in the second stage reaction mixture;

(g) adding dialkyl carbonates to the second stage reaction mixture;

(h) sparging the second stage reaction mixture with carbon dioxide;

(i) adding sources of weakly acidic protons to the second stage reaction mixture.

All percentages, parts and ratios herein are by weight unless otherwise specified. All numerical ranges herein are approximations unless otherwise specified.

A. Reactants, Soap Emulsifiers and Basic Catalysts

1. The Polyol

As used herein, the term "polyol" is intended to include any linear, cyclic, or aromatic compound containing at least four free esterifiable hydroxyl groups. In practicing the improved process disclosed herein, sucrose is the most highly preferred polyol. If sucrose is not used, then the selection of a suitable alternative polyol is simply a matter of choice. For example, suitable polyols can be selected from the following classes: saturated and unsaturated straight and branched chain linear aliphatics; saturated and unsaturated cyclic aliphatics, including heterocyclic aliphatics; or mononuclear or polynuclear aromatics, including heterocyclic aromatics. Carbohydrates and nontoxic glycols are preferred polyols. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol. It is desirable that the aldehyde groups be changed to alcohol groups or reacted with alcohol groups to form ether linkages.

Particularly preferred classes of materials suitable for use herein include the monosaccharides, the disaccharides and sugar alcohols. Preferred carbohydrates and sugar alcohols include xylitol, sorbitol, and sucrose. The most preferred is sucrose.

The use of small particle size polyol, e.g., sucrose, in esterification reactions to form polyol polyesters is highly desirable to improve the speed of reaction. In reactions that use a solvent to form a homogeneous reaction mixture, there is little need for the small particle size, since the polyol is dissolved by the solvent. However, in solventless, heterogeneous reactions of the type herein, the small particle size is highly desirable. The small particle size can also be achieved by art-disclosed methods in which the polyol, e.g., sucrose, is dissolved in water and then the water is removed after the other reactant ingredients and/or catalyst are present to form small particles of the polyol in situ. There is no general consensus, or appreciation, in such art that the primary factor that improves the reaction is the resulting small particle size of the polyol. Furthermore, although this preliminary step of dissolving the polyol in water provides the desired small particle size, it requires the removal of water from the reaction mixture, usually at a time when other ingredients are present, and the presence of water can promote the formation of undesirable side products. It is especially undesirable in a continuous process.

An improved reaction can be achieved without the use of solvent, either in a preliminary step, or in the reaction itself, if the particle size of the solid polyol is less than about 100 microns, preferably less than about 50 microns, more preferably less than about 10 microns. These particle sizes can be achieved, e.g., by a combination of grinding, milling, and/or sieving. It is surprising that the particles of these sizes, prepared by simple mechanical size reduction methods, provide the benefits of the prior art processes requiring formation of water solutions of, e.g., sucrose, that give particle diameters below one micron.

2. Fatty Acid Ester of Easily Removable Alcohol

As used herein, the terms "fatty acid ester(s)" and "ester reactant(s)" are intended to include any compound wherein the alcohol portion is easily removed, including polyols and substituted alcohols, etc., but are preferably esters of volatile alcohols, e.g., the $C_1$–$C_4$ (preferably methyl), 2-methoxy ethyl and benzyl esters of fatty acids containing about eight or more carbon atoms, and mixtures of such esters. Volatile alcohols are highly desirable. Methyl esters are the most highly preferred ester reactants. Suitable ester reactants can be prepared by the reaction of diazoalkanes and fatty acids, or derived by alcoholysis from the fatty acids naturally occurring in fats and oils. Suitable fatty acid esters can be derived from either synthetic or natural, saturated or unsaturated fatty acids and include positional and geometrical isomers. Suitable preferred saturated fatty acids include, for example, acetic, butyric, caproic, caprylic, capric, lauric, myristic, palmitic, stearic, arachidic, behenic, isomyristic, iso-margaric, hydroxystearic, and anteisoarachadic. Suitable preferred unsaturated fatty acids include, for example, myris-toleic, palmitoleic, ricinoleic, linoleic, oleic, elaidic, linolenic, eleosteric, arachidonic, erucic, and erythrogenic acids. Mixtures of fatty acids derived from soybean oil, palm oil, cottonseed oil, safflower oil, rapeseed oil (high erucic acid), canola (low erucic acid), and corn oil are especially preferred for use herein. The fatty acids can be used "as is," and/or after hydrogenation, and/or isomerization, and/or purification. For example, rapeseed provides a good source for $C_{22}$ fatty acid. $C_{16}$–$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, castor oil, safflower seed oil, sesame seed oil, and sunflower seed oil, are examples of other natural oils which can serve as the source of the fatty acid component.

Some useful liquid polyol fatty acid polyesters that can be made according to the improved process of the present invention include liquid sugar fatty acid polyesters, liquid sugar alcohol fatty acid polyesters, and mixtures thereof, the sugars and sugar alcohols containing 4 to 11 hydroxyl groups (preferably from 4 to 8 hydroxyl groups) prior to esterification. These liquid polyol fatty acid polyesters contain at least 4 fatty acid ester groups, preferably no more than 3 unesterified hydroxyl groups, and more preferably no more than 2 unesterified hydroxyl groups. Most preferably, substantially all the hydroxyl groups are esterified with fatty acids, e.g., the liquid sucrose polyesters have from about 7 to 8 hydroxyl groups esterified.

The polyol fatty acid polyesters that are liquid have minimal or no solids at a temperature of 98.6° F. (37° C.), i.e. body temperature. These liquid polyol polyesters typically contain fatty acid ester groups having a high proportion of $C_{12}$ or lower fatty acid groups or else a high proportion of $C_{18}$ or higher unsaturated fatty acid groups. In the case of those liquid polyol polyesters having high proportions of unsaturated $C_{18}$ or higher fatty acid groups, at least about half of the fatty acids incorporated into the polyester molecule are typically unsaturated. Preferred unsaturated fatty acids in such liquid polyol polyesters are oleic acid, elaidic, linoleic acid, and mixtures thereof. The following are non-limiting examples of specific liquid polyol fatty acid polyesters that can be made according to the improved process of the present invention: sucrose tetraoleate, sucrose pentaoleate, sucrose hexaoleate, sucrose heptaoleate, sucrose octaoleate, sucrose hepta- and octaesters of unsaturated soybean oil fatty acids, canola oil fatty acids, cottonseed oil fatty acids, corn oil fatty acids, peanut oil fatty acids, palm kernel oil fatty acids, or coconut oil fatty acids, glucose tetraoleate, glucose tetraesters of coconut oil or unsaturated soybean oil fatty acids, mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

Some useful solid polyol fatty acid polyesters that can be made according to the improved process of the present invention are those wherein the ester groups comprise a combination of: (i) long chain, unsaturated fatty acid radicals and/or short chain saturated fatty acid radicals, and (ii) long chain saturated fatty acid radicals, the ratio of (i):(ii) being from about 1:15 to about 2:1, and wherein at least about 15% (preferably at least about 30%, more preferably at least about 50%, and most preferably at least about 60%) by weight of the total fatty acid radicals in the solid polyol polyester are $C_{20}$ or higher saturated fatty acid radicals. The long chain unsaturated fatty acid radicals are typically, but not necessarily, straight chain (i.e., normal) and contain at least about 12 (preferably about 12 to about 26, more preferably about 18 to 22) carbon atoms. The most preferred unsaturated radicals are the $C_{18}$ mono and/or diunsaturated fatty acid radicals. The short chain saturated fatty acid radicals are typically, but not necessarily, normal and contain 2 to 12 (preferably 6 to 12 and most preferably 8 to 12) carbon atoms. The long chain saturated fatty acid radicals are typically, but not necessarily, normal and contain at least 20 (preferably 20 to 26, most preferably 22) carbon atoms. The molar ratio of Group (i) fatty acid radicals to Group (ii) fatty acid radicals in the polyester molecule is from about 1:15 to about 2:1 (preferably from about 1:7 to about 5:3, more preferably from about 1:7 to about 3:5). The average degree of esterification of these solid polyol fatty acid polyesters is such that at least 4 of the hydroxyl groups of the polyol are esterified. In the case of sucrose polyesters, from about 7 to 8 of the hydroxyl groups of the polyol are preferably esterified. Typically, substantially all (e.g., at least 85%, preferably at least 95%) of the hydroxyl groups of the polyol are esterified.

Some especially useful solid polyol polyesters prepared by the processes herein contain a combination of: (i) long chain (at least 12 carbon atoms) unsaturated fatty acid radicals, or a mixture of said radicals and saturated short chain ($C_2$–$C_{12}$) fatty acid radicals, and (ii) long chain (at least 20 carbon atoms) saturated fatty acid radicals, in a molar ratio of (i) to (ii) of from about 1:15 to about 2:1, and wherein at least four of the hydroxyl groups of the polyol are esterified.

These solid polyol fatty acid polyesters can be used as "thickening agents" or "hardstocks" for blending with liquid digestible or nondigestible oils in the formulation of cooking and salad oils or semi-solid fat products such as shortenings, as well as other food products which contain a combination of fat and non-fat ingredients, e.g., margarines, mayonnaise, frozen dairy desserts and the like. Further, this high capacity to thicken liquid oils makes such compounds, having a melting point above body temperature (37° C.), particularly useful in the formulation of food products containing the nondigestible oils so as to control or prevent the passive oil loss problem associated with the ingestion of such oils.

Examples of long chain unsaturated and polyunsaturated fatty acid radicals for the solid polyol polyesters herein are lauroleate, myristoleate, palmitoleate, oleate, elaidate, erucate, linoleate, linolenate, arachidonate, eicosapentaenoate, and docosahexaenoate. For oxidative stability, the mono- and diunsaturated fatty acid radicals are preferred.

Examples of suitable short chain saturated fatty acid radicals are acetate, butyrate, hexanoate (caproate), octanoate (caprylate), decanoate (caprate) and dodecanoate (laurate). Use of more volatile ester reactants may require modification of the process, e.g., use of reflux in the reactors or other means to prevent excessive loss of said reactants.

Examples of suitable long chain saturated fatty acid radicals are eicosanoate (arachidate), docosanoate (behenate), tetracosanoate (lignocerate), and hexacosanoate (cerotate).

Of course, the long chain unsaturated fatty acid radicals can be used singly or in mixtures with each other or in mixtures with the short chain saturated fatty acid radicals, in all proportions. Likewise, the long chain saturated acid radicals can be used in combination with each other in all proportions. Mixed fatty acid radicals from source oils which contain substantial amounts of the desired unsaturated or saturated acids can be used as the fatty acid radicals to prepare compounds of the invention. The mixed fatty acids from the oils should contain at least about 30% (preferably at least about 50%, and most preferably at least about 80%) of the desired unsaturated or saturated acids. For example, rapeseed oil fatty acids or soybean oil fatty acids can be used instead of pure $C_{12}$–$C_{26}$ unsaturated fatty acids. Hardened (i.e., hydrogenated) high erucic rapeseed oil fatty acids can be used instead of pure $C_{20-26}$ saturated acids. Preferably the $C_{20}$ and higher acids (or their derivatives, e.g., methyl esters) are concentrated, for example by distillation. The fatty acids from palm kernel oil or coconut oil can be used as a source of $C_8$ to $C_{12}$ acids. An example of the use of source oils to make solid polyol polyesters of the invention is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated $C_{18}$ acid radicals to $C_{20}$ and higher saturated acid radicals of about 1:1 and 28.6 weight percent of the total fatty acids in the polyester will be $C_{20}$ and $C_{22}$ fatty acids.

The higher the proportions of the desired unsaturated and saturated acids in the fatty acid stocks used in making the solid polyol polyester, the more efficient the ester will be in its ability to bind liquid oils, including nondigestible oils.

As stated above, some preferred unsaturated fatty acid radicals are those which have 18 carbon atoms, and are mono- and/or diunsaturated. Preferred short chain fatty acid radicals are those which have 8–12 carbon atoms. The preferred long chain saturated fatty acid radical is behenate. Preferred solid polyol polyesters of the invention are polyesters of sucrose in which at least 7 of the 8 hydroxyl groups are esterified.

Examples of such solid polyol polyesters are sorbitol hexaester in which the acid ester radicals are palmitoleate and arachidate in a 1:2 molar ratio; the octaester of raffinose in which the acid ester radicals are linoleate and behenate in a 1:3 molar ratio; the heptaester of maltose wherein the esterifying acid radicals are sunflower seed oil fatty acids and lignocerate in a 3:4 molar ratio; the octaester of sucrose wherein the esterifying acid radicals are oleate and behenate in a 2:6 molar ratio; and the octaester of sucrose wherein the esterifying acid radicals are laurate, linoleate and behenate in a 1:3:4 molar ratio. A preferred material is sucrose polyester in which the degree of esterification is 7–8, and in which the fatty acid radicals are $C_{18}$ mono- and/or diunsaturated and behenic, in a molar ratio of unsaturates:behenic of from about 1:7 to about 3:5.

The said solid polyol polyesters preferably have complete melting points above about 25° C., more preferably above about 37° C., even more preferably above about 50° C. and most preferably above about 60° C. Melting points reported herein are measured by Differential Scanning Calorimetry (DSC). These solid materials have the ability to trap relatively large amounts of oil within their crystal structure. As a consequence, they can be used as "hardstocks" by blending them in amounts of from about 1% to about 50% (typically from about 1% to about 25%) with liquid oils to prepare semi-solid compositions such as shortenings and margarines. A typical suitable range is from about 10% to about 25%. The oils for these compositions can be conventional digestible triglyceride oils such as cottonseed, corn, canola, or soybean oil, or non-digestible edible oils. The solid polyol polyesters of the invention having complete melting points above about 37° C. can be blended at levels of as low as about 1% (preferably at least about 2%) with liquid nondigestible oils having complete melting points below about 37° C. in order to control or prevent passive oil loss upon ingestion of food compositions containing the nondigestible oil. Particularly suitable liquid nondigestible oils are the liquid polyol fatty acid polyesters, in particular the liquid sugar fatty acid polyesters, liquid sugar alcohol fatty acid polyesters, and mixtures thereof, previously described.

Other useful polyol fatty acid polyesters include intermediate melting polyol fatty acid polyesters, in particular intermediate melting sucrose fatty acid polyesters, having certain physical and rheological properties in terms of viscosity and liquid/solid stability. Examples of suitable intermediate melting sucrose fatty acid polyesters are disclosed in, for example, U.S. Pat. No. 4,940,601 to Orphanos et al, issued Jul. 10, 1990 (see, in particular, Column 3, line 50, through Column 5, line 22), and U.S. Pat. No. 4,800,657 to Guffey et al, issued Nov. 14, 1989 (see, in particular, Column 5, lines 22–65), which are incorporated by reference.

As disclosed hereinbefore, other suitable polyol polyesters that can be prepared by the processes herein include the polyol polyesters disclosed in the patents incorporated herein by reference, especially U.S. Pat. Nos.: 3,963,699; 4,517,360; and 4,518,772.

The fatty acid composition (FAC) of the polyol polyesters can be determined by gas chromatography, using a Hewlett-Packard Model 5712A gas chromatograph equipped with a thermal conductivity detector and a Hewlett-Packard Mode 17671A automatic sampler. The chromatographic method used is described in Official Methods and Recommended Practices of the American Oil Chemists Society, 3rd Ed., 1984, Procedures 1-$C_e$62 (incorporated herein by reference).

It is very important for the preparation of improved polyol polyesters that the fatty acid esters be highly purified to remove color/odor materials, oxidation products, and/or their precursors. Such materials include those that have a color, odor, or taste that is objectionable, or which develop an objectionable color, odor, or taste upon heat treatment and/or oxidation. In addition, highly polar materials which coat the catalyst surface should be removed. Preferably, the carbonyl value should be less than about 200 ppm, more preferably less than about 100 ppm, and even more preferably less than about 50 ppm; the free fatty acid level should be less than about 0.1%, more preferably less than about 0.05%, most preferably less than about 0.01%. Processes for preparing such fatty acid esters are disclosed in U.S. Pat. No. 4,931,552 (Gibson et al), issued Jun. 5, 1990, and U.S. Pat. No. 4,942,228 (Gibson), issued Jul. 17, 1990, which are incorporated herein by reference. The percent transmittance at 375 nanometers with a heptane standard should be greater than zero, preferably greater than about 60, most preferably greater than about 80. For typical ester sources without added colored materials, these values define operable reactants. I.e., the carbonyl content is generally indicative of the total level of polar materials present. The low level of color/odor materials and/or oxidation products in the reactants helps provide improved color polyol polyester products.

It is also highly desirable that the fatty acid esters contain little or no difatty ketones and/or β-ketoesters. These by-products can form in the fatty acid esters as a result of contact with basic catalyst during the esterification reaction or with residual basic catalyst during distillation. Improper distillation of the fatty acid esters can also cause difatty ketones and/or β-ketoesters formed to carry-over from the still pot into the distillate. Preferably, the fatty acid esters have about 10 ppm or less difatty ketones and/or β-ketoesters.

An example of one such method for controlling the level of difatty ketones and β-ketoesters in fatty acid methyl esters is as follows:

A vegetable oil (e.g., cottonseed oil) is esterified with methanol in the presence of about 0.25% sodium methoxide. At the end of the esterification reaction, the agitation is stopped, and the glycerin is allowed to separate from the methyl esters by gravity, and is subsequently removed. After the removal of the glycerin, the fatty acid methyl esters are thoroughly mixed with about 15% by weight of water, then the water is allowed to separate by gravity and is removed. The fatty acid methyl esters are then distilled under vacuum at about 220° C.

The water washing is the primary means for controlling the difatty ketone and β-ketoester level in the fatty acid methyl esters. The water removes the basic catalyst which could cause the fatty acid methyl esters to form difatty ketones (DFK) and β-ketoesters (BKE) under the high temperature and low pressure conditions of distillation. The results of some methyl ester-making runs, with and without water washing, are shown below:

| | # of batches | Range (ppm) | Average (ppm) |
|---|---|---|---|
| DFK/BKE level before distillation | 5 | 7–35 | 21.4 |
| DFK/BKE after distillation (without water wash) | 4 | 22–164 | 73.3 |
| DFK/BKE after distillation (with water wash) | 9 | 0–8 | 3.4 |

3. Alkali Metal Fatty Acid Soap

Alkali metal soaps are typically, and preferably, used as emulsifiers in the improved process described herein. For solid polyols, like sucrose, such soaps are believed to be essential. As used herein, the term "alkali metal fatty acid soap" is intended to include the alkali metal salts of saturated and unsaturated fatty acids having from about 8 to about 22 carbon atoms, preferably from about 8 to about 18 carbon atoms. Accordingly, suitable alkali metal fatty acid soaps include, for example, the lithium, sodium, potassium, rubidium, and cesium salts of the fatty acids described hereinbefore. Mixtures of fatty acids derived from soybean oil, sunflower oil, safflower oil, and corn oil are preferred for use herein. Accordingly, preferred alkali metal fatty acid soaps include, for example, the potassium soap made from soybean oil fatty acids.

In a preferred process of reacting sucrose and, especially, the methyl esters of soybean oil fatty acids, it is highly desirable that any soap present be an alkali metal, e.g., potassium or sodium, preferably potassium, salt of hydrogenated fatty acids containing from about 16 to about 22 carbon atoms.

Although some level of soap is typically necessary for optimal performance, especially with solid polyols (e.g. sucrose), the absolute level of soap is desirably kept low, even when there is another emulsifier present. The level of soap should be at least enough to dissolve the polyol at an acceptable rate. Therefore, the level of soap can be reduced as a result of using smaller particle polyol, e.g., sucrose, and/or reaction conditions that favor the solubilization of the polyol. Too much soap can cause excessive foaming. The level of soap in the first stage of the reaction is desirably from about 0.001 to about 0.6, preferably from about 0.2 to about 0.4 moles of soap per mole of polyol. This level of soap assists the polyol, especially sucrose, to dissolve in the reaction mixture. The soap is preferably used in combination with another emulsifier, preferably with the lower esters of the polyol and the fatty acid which are present either by being added as part of the initial reaction mixture, or by backmixing. Also, the soap is preferably potassium soap of hydrogenated fatty acids containing from about 8 to about 22 carbon atoms.

Like the fatty acid ester reactants, it is also highly desirable that the soap contain little or no difatty ketones and/or β-ketoesters. These by-products can form in the soap as the result of contact with basic reagents, such as potassium hydroxide, used during saponification. Preferably, the soap contains about 10 ppm or less difatty ketones and/or β-ketoesters.

4. Basic Catalyst

The basic catalysts generally suitable for use in preparing the polyol polyesters described herein are those selected from the group consisting of alkali metals, such as sodium, lithium and potassium; alloys of two or more alkali metals, such as sodium-lithium and sodium-potassium alloys; alkali metal hydrides, such as sodium, lithium and potassium hydride; alkali metal lower ($C_1$–$C_4$) alkyls such as butyl lithium; and alkali metal alkoxides of lower ($C_1$–$C_4$) alcohols, such as lithium methoxide, potassium t-butoxide, potassium methoxide, and/or sodium methoxide. Potassium methoxide is preferred, especially when used with potassium soap. Certain basic catalysts, such as sodium and potassium hydride, are particularly prone to generate difatty ketones and/or β-ketoesters.

Another particularly preferred basic catalyst is potassium carbonate, sodium carbonate, barium carbonate, or mixtures of these compounds having particle sizes that are less than about 100 microns, preferably less than about 50 microns, as discussed more fully hereinafter. It has been found that when these specific compounds are used as catalysts, increased yields of light colored higher polyol polyesters are obtained when compared to essentially identical reactions carried out using more conventional catalysts, such as sodium hydride, potassium hydride, soap, or sodium methoxide. These preferred catalysts can also be used in admixture with the more conventional basic catalysts, described above. Potassium carbonate and/or potassium methoxide are the most preferred catalysts for use herein. The use of these catalysts is further disclosed in U.S. Pat. No. 4,517,360 (Volpenhein), issued May 14, 1985, which is incorporated herein by reference.

More reactive catalysts such as potassium or sodium methoxide can be protected until their addition into the reaction mixture. Preferably the catalyst should be suspended in or more preferably encapsulated by a material that will either be present in the reaction mixture or be readily separated from the reaction mixture. Suitable encapsulating agents include said alkyl esters of, e.g., $C_{16}$–$C_{22}$ fatty acids. (As described hereafter, these catalysts can also be protected when prepared from and stored in a lower ($C_1$–$C_4$) alcohol, such as methanol, under anhydrous conditions.) Addition of these more alkaline, reactive catalysts in the second stage of the reaction after the polyol has an average degree of esterification of more than about 60%, preferably more than about 85%, provides improved reaction kinetics and results in a greater degree of esterification of the polyol yet does not create the level of color/odor materials that would be created if such catalysts were present from the start of the reaction.

The level of catalyst is kept as low as possible, particularly in the second stage of the reaction, as discussed more fully hereafter, typically in the range of from about 0.01 to about 0.5, preferably from about 0.01 to about 0.1, more preferably from about 0.02 to about 0.05, moles of catalyst per mole of polyol. The level of catalyst can be lowered to the least amount that is effective to give a reasonable rate of reaction. It is possible to have very fast reactions using only the residual base in, e.g., the soap emulsifier commonly used in such reactions. It is desirable to keep the level of base as low as possible to minimize formation of color and/or odor bodies and/or excess soap and/or by-products. It is also desirable to effect the removal of oversize catalyst after the first stage of the reaction, and/or the destruction and removal of the catalyst after the reaction has reached the desired end point.

B. First Stage Reaction Conditions to Obtain Polyol Fatty Acid Lower Esters

In the first stage of the improved solvent-free transesterification process of the present invention, polyol fatty acid partial esters are formed from a heterogeneous reaction mixture containing the polyol, at least a portion of the fatty acid esters of the easily removable alcohol, an effective amount of the basic esterification catalyst, and optionally, but preferably, a soap emulsifier. The precise ratio of these reactants can be freely selected from within the guidelines previously described. However, some routine experimentation can be necessary in order to establish the optimum ratios for a given set of reactants. The first stage reaction mixture can be formed in a solvent-free manner or by using a solvent such as water to dissolve one or more of the reactants (e.g., sucrose), followed by removal of the solvent before carrying out the first stage reaction.

This first stage reaction mixture is then heated to an appropriate temperature to provide a melt in which the polyol and the fatty acid esters of the easily removable alcohol react to form polyol fatty acid partial esters. As used herein, the term "polyol fatty acid partial esters" are those esters of the polyol wherein up to about 50% of the hydroxy groups of the polyol have been esterified. In the case of sucrose, the primary sucrose fatty acid partial esters are the mono-, di- and/or triesters. The end of the first stage of the reaction is usually determined by measuring the level of unreacted polyol in the reaction mixture. In the case of sucrose, the end of the first stage typically occurs when the level of unreacted sucrose is less than about 1%.

This first stage reaction mixture is typically heated to temperatures of from about 265° to about 285° F. (from about 129.4° to about 140.6° C.), preferably to from about 270° to about 275° F. (from about 132.2° to about 135° C.). These reaction temperatures typically achieve a rapid initial esterification of the polyol to form the polyol fatty acid partial esters without excessive degradation of the polyol. The first stage reaction is also desirably carried out under a pressure of from about 1 to about 100 mm Hg, preferably from about 5 to about 50 mm Hg.

After the average degree of esterification reaches about 60%, the soap emulsifier is no longer needed to facilitate the reaction and, therefore, can be removed. The soap emulsifier is not essential after the polyol has reacted once and there is sufficient partial ester to maintain the homogeneity of the reaction mixture.

Removal of soap can be accomplished, e.g., by filtration, centrifugation, etc., since the soap is relatively insoluble in the reaction mixture at higher degrees of esterification. The filtered reaction mixture typically has a soap level of less than about 0.5, preferably less than about 0.1 moles of soap per mole of polyol, more preferably less than about 0.05 moles of soap per mole of polyol. The filtered material can be used as a reactant in the first stage reaction mixture. However, since the composition of the filtered material can vary, it is usually better not to recycle it.

Removal of the soap is not desirable at the early part of the first stage reaction, especially when the preferred low levels of soap described herein are used. However, especially after esterification of the polyol is about 60% complete, any soap that is not soluble in the reaction mix can be removed advantageously.

Unreacted polyol and/or large particle catalyst are also desirably removed before the polyol is esterified to more than about 75% and, preferably, (a) after the degree of esterification is greater than about 15%, preferably greater than about 40%, and (b) while the soap that is present is still soluble in the reaction mixture. This removal results in fast reaction kinetics and high conversion to highly esterified product having good color without the need to add additional catalyst thereafter, and is accordingly, especially desirable in a continuous process. Removal at an early point is more convenient than at a later point due to the low viscosity of the reaction mixture and minimizes production of unwanted by-products. Unreacted polyol, such as sucrose, can interfere with the orderly progress of the second stage of the reaction where it limits the desired interesterification reaction by degrading, and/or preferentially reacting with, the active form of the catalyst and/or by continuing to create undesirable by-products such as color bodies and/or interesterifying with highly esterified polyol fatty acid polyesters.

Removal of unreacted polyol and/or large size catalyst can be accomplished by, e.g., filtration and/or by centrifugation if the polyol is a solid in the reaction mixture. The resulting reaction mixture that is free of unreacted polyol will then react faster and reach the desired degree of esterification quicker than if the polyol remains. The reaction mixture obtained by, e.g., filtration, typically has an unreacted polyol content of less than about 1%, preferably less than above 0.2%, and more preferably less than about 0.05%. The filtered polyol and/or catalyst can be used as a reactant or else discarded.

Unreacted polyol is preferably removed at a point in the reaction while any soap emulsifier is still soluble in the reaction mixture. When the polyol is removed at an early stage, the molar ratio of soap emulsifier to polyol either remains essentially unchanged, or is slightly increased.

It is highly desirable to conduct the first stage reaction under back-mixing conditions to maintain the degree of esterification between about 10% (preferably 20%) and about 70%, preferably between about 35% and about 60%. This degree of esterification provides sufficient polyol fatty acid partial esters to aid in the solubilization of the poorly soluble polyol and to provide a stable heterogeneous reaction mixture that minimizes unreacted polyol, and the distribution/composition and/or level of partial esters and/or soap that cause foaming is low enough to permit a continuous reaction without overfoaming. In a continuous reaction, the individual reactants can be added to the first stage at a rate that maintains the desired degree of esterification and yet provides sufficient yield from the first stage to maintain the reaction in the subsequent second stage.

Backmixing can be achieved in a continuous reaction, for example, by continually recycling a portion of the first stage reaction stream and/or by carrying out the reaction in a well agitated vessel (or, e.g., two vessels in series, or any other similar configuration that has hydrodynamically similar mixing conditions) where the reactants are continually added and the product is removed at rates that maintain the desired level of esterification. Although it is possible to start with plug flow conditions, the initial solubility of sucrose is low at the start of the reaction; the risk of unacceptable levels of foam when the degree of esterification is less than about 20% is great; and the resulting instability of the reaction mixture gives variable, poorly controlled esterification of the polyol. Without filtration of the unreacted reactants as discussed hereinbefore, the conversion of the polyol can be poor and therefore plug flow is undesirable in the first stage, especially without recycling.

The product of the first stage is preferably filtered, as discussed hereinbefore, and the unreacted solids are returned as reactants, or, preferably, if at a lower level, discarded, since the ingredients are present, at least initially, at varying and unknown levels. If the reaction mixture contains only low levels of soap emulsifier and catalyst, as preferred herein, the amount of material to be separated is minimal. Once steady state is achieved in a continuous reaction, the separated material can be cleaned up, e.g., by a purge stream, and recycled.

Backmixing in a batch process can be approximated by using part of a previous batch that has the right degree of esterification, and adding reactants to the batch while the reaction is continuing until the appropriate degree of completion is reached, whereupon the addition of reactants is stopped and the reaction is taken to completion. A "semi-batch" reaction can be run by continually bringing batches to the appropriate intermediate degree of completion and then transferring at least the major portion of the batch to another vessel where the reaction is taken to completion.

Apparatus that is suitable for backmixing, and/or plug flow conditions, as discussed hereinafter, is disclosed in U.S. Pat. Nos.: 3,567,396, Setzler, issued Mar. 2, 1971; 3,679,368, Balint, et al., issued Jul. 25, 1972; 4,449,828, Mansour, issued May 22, 1984; 4,472,061, Mansour, issued Sep. 18, 1984; 4,543,194, Spence et al., issued Sep. 24, 1985; and 4,615,870, Armstrong et al., issued Oct. 7, 1986, all of said patents being incorporated herein by reference. Other disclosures of suitable processes and apparatus can be found in: The Degree of Mixing in Continuous Flow Systems, Zwietering, Chemical Engineering Science, pp. 1–15, Vol. II, No. 1 (1959); Continuous Flow Stirred-Tank Reactor Systems, MacDonald and Piret, Chemical Engineering Progress, Vol. 47, No. 7, pp. 363–8 (July 1951); and Reaction Kinetics in a Tubular Reactor, Baron, Manning and Johnstone, Chemical Engineering Progress, Vol. 48, No. 3, pp. 125–132 (March 1952), all of said articles being incorporated herein by reference.

C. Second Stage Reaction Conditions to Obtain Highly Esterified Polyol Fatty Acid Polyesters In the second stage of the improved solvent-free transesterification process of the present invention, highly esterified polyol fatty acid polyesters are formed from a reaction mixture containing the polyol fatty acid partial esters, the remaining portion of the fatty acid esters of the easily removable alcohol, and an effective amount of a basic catalyst. This remaining portion of fatty acid esters can be obtained by including an excess thereof in the first stage reaction mixture, i.e. an amount beyond that required to form polyol fatty acid partial esters ("single-step" addition). However, the remaining portion of the fatty acid esters required to obtain highly esterified polyol fatty acid polyesters is typically added to the reaction mixture resulting from the first stage of the reaction ("two-step" addition).

The reaction mixture resulting from the first stage of the reaction can contain sufficient basic catalyst for the purposes of the second stage of the reaction. However, more basic catalyst can be added, if needed. This additional basic catalyst can be the same as the basic catalyst used in the first stage of the reaction, or can be a different basic catalyst.

During the second stage of the reaction, the polyol fatty acid lower esters and the remaining portion of the fatty acid esters react to provide highly esterified polyol fatty acid polyesters. As used herein, the term "highly esterified polyol fatty acid polyesters" refers to a polyol wherein at least about 50%, preferably at least about 70%, and most preferably at least about 96%, of the hydroxy groups are esterified. In the case of highly esterified sucrose polyesters, this typically refers to the hexa-, hepta-, and particularly octa-esters. For example, if at least about 96% of the hydroxy groups of sucrose are esterified, at least about 70% of the sucrose esters are sucrose octaesters.

The second stage of the reaction should be carried out under plug-flow, or batch, conditions to prevent backmixing and thereby achieve high degrees of esterification. This plug flow can be approximated by feeding the output of the first stage into a series of at least two continuous stirred tank reactors (i.e. a continuous reactor), for example, in a tubular reactor and/or packed column and/or tray reactor and/or falling or rising film reactor, using more nearly plug-flow reactor apparatus. As discussed hereinbefore, the plug-flow conditions should be used after the degree of esterification of said polyol has reached at least about 50%. The final degree of esterification should be at least about 70%, preferably at least about 96%.

1. Primary reaction conditions for reducing the level of difatty ketones and β-ketoesters The improvement in the transesterification process according to the present invention is to carry out the second stage reaction under conditions that reduce the combined level of difatty ketones and β-ketoesters to about 300 ppm or less, preferably about 200 ppm or less, most preferably about 100 ppm or less, in the resulting highly esterified polyol fatty acid polyesters, after residual fatty acid esters, basic catalyst and soap emulsifier have been removed. As used herein, the terms "difatty ketones" and "β-ketoesters" typically refer to moieties that have at least 15 and at least 16 carbon atoms, respectively. (The method for measuring difatty ketones/β-ketoesters according to the present invention is described hereafter in the Analytical Methods section. This method cannot distinguish between difatty ketones formed during the second stage reaction and those formed as a result of β-ketoesters being converted to difatty ketones during analytical preparation. Accordingly, all values referred to herein are in terms of combined levels of difatty ketones and β-ketoesters.).

Two primary reaction conditions are used in the second stage reaction to reduce the level of difatty ketones and/or β-ketoesters: (a) controlling the level of easily removable alcohol in the liquid phase of the second stage reaction mixture to from about 10 to about 150 ppm, preferably from about 20 to about 100 ppm; and (b) heating the second stage reaction mixture to temperatures in the range of from about 175° to about 275° F. (from about 79.4° to about 135° C.), preferably from about 210° to about 250° F. (from about 98.9° to about 121.1° C.).

The easily removable alcohol is typically generated as a result of the esterification of the polyol with the fatty acid esters. The level of easily removable alcohol present in the liquid phase of the second stage reaction mixture can be controlled by a variety of methods or combinations of methods. (The method for measuring the level of alcohol in the liquid phase of the second stage reaction mixture according to the present invention is described hereafter in the Analytical Methods section.) One particularly preferred method is by controlling the reaction pressure. A pressure of at least about 15 mm Hg (typical range of from about 15 to about 100 mm Hg) is suitable for controlling the level of easily removable alcohol within the previously indicated range of from about 10 to about 150 ppm. A pressure of at least about 30 mm Hg (typical range of from about 30 to about 50 mm Hg) is suitable for controlling the level of easily removable alcohol within the previously indicated preferred range of from about 20 to about 100 ppm.

Another suitable method for controlling the level of easily removable alcohol is by appropriate agitation of the second stage reaction mixture. Suitable agitation conditions include nitrogen sparging of the second stage reaction mixture, and proper design of the agitator to control the removal of alcohol from the liquid phase to the vapor phase at an appropriate rate. In addition, appropriate adjustment of the agitator speed can greatly aid in controlling the level of easily removable alcohol present in the liquid phase. What agitator speed is appropriate can depend on the size and shape of both the agitator and the reactor. Some routine experimentation may be necessary in order to establish the appropriate agitator speed for a given system. The combination of pressure control, as previously described, together with nitrogen sparging, is a particularly preferred method for controlling the level of easily removable alcohol in the liquid phase of the second stage reaction mixture according to the present invention.

Another method for controlling the level of easily removable alcohol is by an appropriate design in the size and shape of the reactor used in carrying out the second stage reaction. Suitable reactor sizes and shapes for controlling the level of easily removable alcohol are determined by the mass transfer rate. For example, in small, laboratory scale systems, spherical, cylindrical or column reactors have suitable mass transfer rates, provided there is a proper combination of stirring (agitation) and reaction pressure. As the reactor increases in size, systems that increase the mass transfer surface area can be advantageously used, including, but not limited to, cylindrical reactors with proper agitation procedures, column reactors having trays or packing, and column reactors where the reactants are spread out as a thin film over the surface of the column.

2. Optional Reaction Conditions for Reducing the Level of Difatty Ketones and β-ketoesters In addition to the two primary reaction conditions for reducing the formation of difatty ketones and β-ketoesters, one or more of the following optional reaction conditions can also be used during the second stage reaction to achieve a further reduction in the level of these by-products:

c. Keeping the molar ratio of fatty acid esters of the easily removable alcohol, to each esterifiable hydroxy group of the polyol in the second stage reaction mixture in the range of from about 0.9:1 to about 1.4:1, preferably from about 0.9:1 to about 1.2:1.

The molar ratio of fatty acid esters of the easily removable alcohol, to each esterifiable hydroxy group of the polyol, can be kept within the indicated range of from about 0.9:1 to about 1.4:1 (preferably from about 0.9:1 to about 1.2:1) by any appropriate method. (As used herein, the term "esterifiable hydroxy group" refers to the total number of hydroxy groups on the polyol prior to esterification.) One particularly preferred method for keeping this molar ratio within the indicated range is by continuously adding the fatty acid esters in an incremental fashion to the second stage reaction mixture such that the molar ratio of fatty acid esters to remaining, unesterified hydroxy groups is kept at about 1:1 until the esterification reaction is at least about 95% complete. This continuous incremental metering in of fatty acid esters is particularly desirable in permitting higher yields of highly esterified polyol fatty acid polyesters while at the same time minimizing the formation of difatty ketones and/or β-ketoesters.

d. Removing materials having particle sizes greater than about 1 micron when the transesterification reaction reaches from about 50 to about 75% of completion The benefits of removing large size particles with regard to unreacted polyol, catalyst and soap-emulsifier have previously been mentioned. However, it is also believed that the removal of particles larger than about 1 micron in size when the transesterification reaction reaches from about 50 to about 75% of completion will cause the removal of insoluble fatty acid ester anion precursors to β-ketoesters. Removal of particles larger than about 1 micron in size can be achieved by a any suitable method, and preferably is achieved by the use of filtration.

e. Using alkali metal alkoxides of lower alcohols that have been prepared and remain dissolved in the respective lower alcohol As previously indicated, the alkali metal alkoxides of lower ($C_1$–$C_4$) alcohols, such as lithium methoxide, potassium methoxide and sodium methoxide, are more active catalysts. These more active catalysts are particularly preferred in the second stage reaction. However, the use of these more active catalysts, in an unprotected state, can increase the formation of difatty ketones and/or β-ketoesters. It has been found that when these alkali metal alkoxide catalysts are prepared from and remain dissolved in the respective lower alcohol, their use in the second stage reaction does not result in increased formation of difatty ketones and/or β-ketoesters.

f. Reduced levels of basic catalyst

The use of higher levels of basic catalyst, in particular the alkali metal alkoxides of lower alcohols, tends to increase the formation of difatty ketones and/or β-ketoesters during the second stage reaction. Accordingly, while the use of lower levels of basic catalyst is desirable during the first stage reaction, it is particularly desirable in the second stage reaction to reduce the formation of difatty ketones and/or β-ketoesters, such as by filtration and removal of particles larger than about 1 micron as previously described. The preferred level of basic catalyst used during the second stage reaction is from about 0.01 to about 0.1, more preferably from about 0.02 to about 0.05, moles per mole of polyol. Even with these lower levels of basic catalyst, the second stage reaction proceeds at a sufficiently fast rate to obtain the desired yields of highly esterified polyol polyesters.

g. Adding dialkyl carbonates

The use of dialkyl carbonate during the second stage reaction has also been found to retard the formation of β-ketoesters, possibly by acting as a trap or scavenger for the fatty acid ester anions. Suitable dialkyl carbonates that can be added to the second stage reaction mixture include $C_1$–$C_4$ dialkyl carbonates such as dimethyl carbonate, diethyl carbonate, dipropyl carbonate and di-tert-butyl carbonate. The amount that can be added to the second stage reaction mixture is from about 0.1 to about 1000, preferably from about 0.1 to about 100, moles of dialkyl carbonate per mole of polyol.

h. Sparging with carbon dioxide

As previously mentioned, difatty ketone formation is believed to be due to the fact that the β-ketoesters formed lose carbon dioxide (decarboxylate). Since this decarboxylation is reversible, the addition (e.g., sparging) of carbon dioxide (or a compound capable of in situ formation of carbon dioxide) in the second stage reaction mixture can be used to suppress difatty ketone formation, i.e. by converting it back to β-ketoesters that can reversibly convert back to fatty acid esters. (Like the addition of dialkyl carbonates, carbon dioxide sparging may also act as a trap or scavenger for the fatty acid ester anions.) The second stage reaction mixture can be sparged with from about $1\times10^{-4}$ to about $1\times10^{-2}$, preferably from about $4\times10^{-4}$ to about $4\times10^{-3}$, moles of carbon dioxide per mole of polyol. This carbon dioxide sparging preferably occurs at a rate such that the previously described quantities of carbon dioxide are used during the course of the second stage reaction.

i. Adding sources of weakly acidic protons

As previously mentioned, the fatty acid ester anions are precursor to β-ketoesters. In order to suppress fatty acid ester anion formation, a source of weakly acidic protons can be added to the second stage reaction mixture. Suitable sources of weakly acidic protons have pKas of from about 9 to about 20 and include sucrose partial esters (from either commercially available sources or from materials filtered out after the first stage reaction), sucrose solubilized in sucrose partial esters and/or soap, and alkali metal bicarbonates such as sodium and preferably potassium bicarbonate. These sources of weakly acidic protons can be added to the second stage reaction mixture at a level of from about 0.001 to about 10, preferably from about 0.01 to about 1, per mole of polyol.

3. Importance of combinations of primary and optional reactions conditions to minimize difatty ketone/β-ketoester formation while maximizing Polyester formation Each of the primary reaction conditions (i.e. controlling alcohol level and temperature) and optional reaction conditions will achieve some reduction in the formation of a difatty ketones and/or β-ketoesters during the second stage reaction. However, it has been found that the combination of primary reaction conditions with one or more optional reactions conditions during the second stage reaction can achieve a maximum reduction in the level of difatty ketones and/or β-ketoesters, while at the same time maximizing the yield of desired highly esterified polyol fatty acid esters (e.g., sucrose octaesters) obtained, particularly if the second stage reaction is carried out in larger, commercial scale reactors. This is necessitated by the fact that those conditions which favor the reduction of difatty ketones/β-ketoester formation also tend to minimize the yield of highly esterified polyol polyesters. Indeed, the reaction kinetics involved in certain of the primary and optional reaction conditions tend to more greatly affect the rate of β-ketoester formation, compared to the rate of polyol polyester formation.

For example, with regard to the level of easily removable alcohol present in the liquid phase of the second stage reaction mixture, it has been found (to a first approximation)

that the rate of polyol polyester formation is inversely proportional to the alcohol concentration, while the rate of β-ketoester formation is inversely proportional to the square of the alcohol concentration. This means that, while increasing the level of alcohol present will decrease the rate of polyol polyester formation, there will be a much greater decrease in the rate of β-ketoester formation.

By comparison, changes in the molar ratio of fatty acid esters with respect to the polyol have different reaction kinetics but a similar effect. Specifically, the rate of polyol polyester formation has been found (to a first approximation) to be directly proportional to the concentration of fatty acid esters, while the rate of β-ketoester formation has been found to be directly proportional to the square of the concentration of fatty acid esters. As in the case of alcohol concentration, decreasing the concentration of fatty acid esters (and thus increasing the molar ratio with respect to the polyol) has a much greater effect on the rate of β-ketoester formation than it does on the rate of polyol polyester formation.

D. Analytical Methods

1. Alcohol in liquid phase of reaction mixture

In measuring the amount of easily removable alcohol present in the liquid phase of the second stage reaction mixtures, the sample should be obtained and maintained under the pressure conditions existing in the second stage reaction until just prior to analysis. During the second stage reaction, the reaction mixture is typically under a vacuum. One way of obtaining and maintaining the sample under vacuum is to use a small tube that extends from the inside to the outside of the reactor. The end of the tube inside the reactor is inserted under the liquid level of the reaction mixture. The end of the tube outside the reactor is then inserted into a small sealed container having a premeasured volume and weight; the container also has a magnetic stir bar inside of it and a septum at one end. The portion of the tube outside the reactor has a series of clamps and/or valves that permit the container to be disconnected from the tube without altering the vacuum in the container or the reactor. A small pump for pumping the sample from the reactor to the container can also be used. Prior to attachment to the tube, the container is either placed under a vacuum or purged with nitrogen. The container is then connected to the tube, and the clamps and/or valves are opened to permit the pressure in the container to equalize with that in the reactor. When needed, the desired amount of sample can be pumped into the container; alternatively, in the absence of a pump, the reaction pressure can be momentarily raised very slightly to provide a pressure differential between the reactor and the container to obtain the sample. The clamps and/or valves are then closed and the container with sample disconnected while being maintained under vacuum. The container is weighed to determine the exact amount of sample collected. The container is then heated to about 60° C. and magnetically stirred, while still sealed, to evaporate the alcohol present in the liquid phase into the headspace of the container. At this point, nitrogen is carefully introduced into the container to equalize the pressure therein to atmospheric. A syringe is then inserted into the septum of the container, and a precise volume of vapor in the headspace is obtained. The amount of alcohol in this headspace sample can then be analyzed conveniently by gas chromatography using a packed column (Chromasorb 101) and an internal standard (i.e. isopropane). This method is calibrated by determining the amount of methanol in the headspace of a standard sample having a known concentration of methanol in the liquid phase.

2. Difatty ketones/β-ketoesters in reaction mixture

In measuring the level of difatty ketones/β-ketoesters in the reaction mixture, a sample from the reaction mixture is mixed with a tetracosane internal standard. Alkaline alumina (10% KOH and 15% $H_2$) is added to the sample and internal standard, and then the entire mixture is heated to saponify all saponifiable components. (Saponification also converts any β-ketoesters present to difatty ketones.) After saponification, the mixture is cooled and then transferred to a chromatographic column along with dichloromethane as the solvent. The solvent elutes the difatty ketones, the internal standard and other unsaponifiable components from the alumina in the column. The solvent is then evaporated and the residue analyzed for difatty ketones/β-ketoesters by an internal standard gas chromatographic method using a 15 m. long fused silica capillary column (DB-1 25 micron film thickness, 0.25 mm. inside diameter).

E. Specific Illustrations of Improved Process According to Present Invention The following are specific illustrations of the improved process according to the present invention:

EXAMPLE 1

The reactor train consists of five continuous, stirred, tank reactors (CSTR's). Each reactor is a well-agitated, 25 gallon vessel with an external recycle loop that has a pump rate of about 0.3 reactor volumes per minute. The reactors are operated with the following approximate conditions:

| Parameter | Reactor Number | | | | |
| --- | --- | --- | --- | --- | --- |
| | 1 | 2 | 3 | 4 | 5 |
| Residence Time (hr) | 1.5 | 1.5 | 2.0 | 2.0 | 2.0 |
| Temperature (° C.) | 135.0 | 135.0 | 120.0 | 120.0 | 120.0 |
| Pressure (mm Hg) | 15.0 | 15.0 | 40.0 | 40.0 | 40.0 |
| $N_2$ Sparge (lb/hr) | 0.0 | 0.0 | 2.4 | 2.4 | 2.4 |

The sparge rate can vary from about 0.01 to about 1 lb. of $N_2$ per lb. of polyol. Similar sparge rates can be used for other gases and other polyols, using substantially equivalent moles of gas per esterfiable hydroxy group on the polyol.

The feed mixture is composed of partially hardened soybean methyl esters (about 79% by wt.), a reduced level of potassium stearate soap (about 3% by wt.), and sucrose whose average particle size has been reduced to an average that is less than about 100 microns (about 17% by wt.). An approximately 25% slurry of potassium carbonate in partially hardened methyl esters is continuously introduced into the first two reactors during continuous operation to maintain the catalyst level at about 0.3–0.6%.

To start up the system, the first reactor is started up in a batch mode using approximately 19 liters of the feed slurry and about 250 ml of the catalyst slurry. The batch reactor conditions are about 135° C. and about 15 mm Hg. Once the average composition of the product reaches about two fatty acid chains per molecule of sucrose and contains about 6% sucrose, the batch operation is stopped and the continuous operation is started with the feed slurry introduced into the first reactor and the intermediate product from the first reactor cascading to the second and so on down the train.

Filtration of the residual, unreacted sucrose is employed between the second and third reactors. Filtration is accomplished by feeding the material through a cartridge filter so that all particles greater than 1 micron are filtered out.

Following filtration, there is no recatalysis. If faster reactions are desired, additional catalyst ($K_2CO_3$) slurry, or $KOCH_3$ can be added. A separate stream of partially hardened methyl esters is introduced into both the second and third reactors of the reactor train such that, after addition, the total molar ratio of methyl esters to sucrose is about 10:1 (i.e. a total molar ratio of methyl esters to esterifiable hydroxy groups of about 1.25:1). The reactors are allowed to reach steady-state with the average composition at steady-stage exiting from each reactor being about the following:

|  | Reactor Number | | | | |
| --- | --- | --- | --- | --- | --- |
| Parameter | 1 | 2 | 3 | 4 | 5 |
| Average Fatty Acid Chains per Molecule of Sucrose | 2.7 | 3.8 | 6.3 | 7.7 | 7.9 |
| Soap (Wt. %) | 3.0 | 2.2 | 1.8 | 1.8 | 1.8 |
| Catalyst (Wt. %) | 0.3 | 0.3 | 0.3 | 0.3 | 0.3 |
| Sucrose (Wt. %) | 4.2 | 1.4 | <0.1 | <0.1 | <0.1 |

The combination of reduced sucrose particle size and the CSTR orientation for the first stage of the reaction achieves excellent sucrose utilization at reduced soap levels.

The combination of sucrose filtration, lower soap levels, and high $N_2$ sparging rates achieves fast and robust reactions that reliably reach high levels of reaction completion. These combined improvements also allow the use of higher pressures, lower temperatures and reduced ester:sucrose ratios, thus improving process economics and product quality. Similar results are achieved when a trayed column reactor, or other plug flow reactor, is substituted for the last three reactors.

Following the reaction, the soap and catalyst are removed by centrifugation. The excess methyl esters are evaporated from the sucrose polyester using a thin film evaporator. Finally, low levels of color/odor/flavor bodies as well as residual low levels of fatty acid esters are removed by steam deodorization.

This set of operating conditions typically yields a product that is at least about 75% sucrose octaester and contains about 200 ppm or less combined di-fatty ketone and β-ketoester.

EXAMPLE 2

The reaction is conducted in a 1 liter spherical glass reaction vessel. The temperature is controlled by means of a heating mantle, thermometer, and temperature controller. The reaction pressure is controlled by means of a vacuum pump and a Cartesian mercury manostat. The agitation is controlled by means of a constant speed stirrer with a torque sensor that maintains a constant RPM without regard to changes in liquid viscosity. Additionally, the stirrer is connected to a voltage regulator which provides constant voltage to the stirrer regardless of variations in building voltage. Methanol from the liquid reaction mixture is measured by the analytical method described in section D(1).

About 34.2 grams of finely powdered sucrose are added to the reactor along with about 1.4 grams of powdered potassium carbonate, about 24 grams of potassium soap and about 146 grams of partially hardened soybean methyl esters (Iodine Value of about 55). The mixture is heated to about 135° C., under a pressure of about 15 mm Hg with about 600 RPM agitation for about 1.5 hours. At the end of this period, about 205 additional grams of partially hardened soybean methyl esters and about 1.4 additional grams of powdered potassium carbonate are added to the reactor. The reaction is continued at about 135° C., about 0.5 mm Hg pressure, and about 600 RPM of agitation for an additional 5 hours. The results of this reaction in terms of sucrose hydroxyl groups that have been esterified (% Esterification), difatty ketone/β-ketoester (DFK/BKE) level in the unrefined reaction product and methanol in the liquid reaction mixture (Methanol) are shown below.

| % Esterification | Methanol (ppm) | DFK/BKE (ppm)* |
| --- | --- | --- |
| 97.4 | 8.7 | 608 |
| 98.4 | 7.6 | 738 |
| 98.6 | 4.5 | 778 |

*In unpurified, crude product

The same reactor and reaction conditions are used as above, except, after the first 1.5 hours of reaction, the reaction pressure is about 15 mm Hg, and about 20 standard cubic centimeters per minute of nitrogen is bubbled through the reaction mixture. The results are shown below:

| % Esterification | DFK/BKE (ppm)* |
| --- | --- |
| 94.9 | 202 |
| 96.6 | 331 |
| 98.0 | 482 |
| 98.8 | 469 |

*In unpurified, crude product

EXAMPLE 3

The same reactor and reaction conditions are used as in Example 2, except after the first 1.5 hours of reaction, the reaction pressure is about 30 mm Hg, and about 20 standard cubic centimeters per minute of nitrogen is bubbled through the reaction mixture. The results are shown below:

| % Esterification | Methanol (ppm) | DFK/BKE (ppm)* |
| --- | --- | --- |
| 95.0 | 123 | 94 |
| 95.3 | 35 | 93 |
| 96.0 | 16 | 106 |
| 96.4 | 20 | 96 |

*As in Example 2

EXAMPLE 4

The same reactor and reaction conditions are used as in Example 2, except after the first 1.5 hours of reaction, the reaction pressure is about 30 mm Hg, about 20 standard cubic centimeters per minute of nitrogen is bubbled through the reaction mixture, and the reaction temperature after 1.5 hours of reaction is reduced to 110° C. The results are shown below:

| % Esterification | DFK/BKE (ppm)* |
| --- | --- |
| 96.6 | 90 |
| 98.5 | 157 |

-continued

| % Esterification | DFK/BKE (ppm)* |
|---|---|
| 98.6 | 174 |
| 98.7 | 201 |

*As in Example 2

EXAMPLE 5

For the following four reactions (5A through 5D), the same reactor and reaction conditions are used as in Example 2, except that the agitation speed is changed to show its effect on DFK/BKE levels. The results are shown below:

| Reaction | % Esterification | Stirrer RPM | Methanol (ppm) | DFK/BKE (ppm)* |
|---|---|---|---|---|
| 5A | 98.0 | 350 | 15.2 | 386 |
| 5B | 98.8 | 500 | not measured | 540 |
| 5c | 98.6 | 600 | 4.5 | 778 |
| 5D | 99.0 | 680 | 3.0 | 977 |

*As in Example 2

What is claimed is:

1. In a solvent-free, two-stage transesterification process for preparing highly esterified polyol fatty acid polyesters from a polyol and fatty acid esters of an easily removable alcohol, wherein said first stage comprises forming polyol fatty acid partial esters from a reaction mixture containing a polyol having at least 4 esterifiable hydroxy groups and the fatty acid esters of the easily removable alcohol in the presence of an effective amount of a basic catalyst and optionally an effective amount of soap emulsifier, and wherein said second stage comprises forming highly esterified polyol fatty acid polyesters from a reaction mixture containing the polyol fatty acid partial esters, fatty acid esters of the easily removable alcohol and an effective amount of a basic catalyst, the improvement which comprises carrying out said second stage under reaction conditions that provide a combined level of difatty ketones and β-ketoesters of about 300 ppm or less in the resulting highly esterified polyol fatty acid polyesters, and that result in at least about 96% of the hydroxy groups of the polyol being esterified, said reaction conditions including:
    (a) controlling the level of easily removable alcohol in the liquid phase of the second stage reaction mixture to from about 10 to about 150 ppm; and
    (b) heating the second stage reaction mixture to temperatures in the range of from about 79.4° C. to about 135° C. and a pressure of from about 15 to about 100 mm Hg; and
    (c) sparging with an inert gas; and
    (d) keeping the molar ratio of fatty acid esters of easily removable alcohols to each esterifiable hydroxy group of the polyol in the range of from about 0.91 to about 1.4:1.

2. The process of claim 1 wherein the polyol is sucrose.

3. The process of claim 2 wherein the combined level of difatty ketones and β-ketoesters in the resulting highly esterified polyol fatty acid polyesters is about 200 ppm or less.

4. The process of claim 3 wherein the combined level of difatty ketones and β-ketoesters is about 100 ppm or less.

5. The process of claim 4 wherein the second stage reaction mixture is agitated.

6. The process of claim 4 wherein said second stage reaction conditions include:
    (a) controlling the level of easily removable alcohol in the liquid phase of the second stage reaction mixture to from about 20 to about 100 ppm; and
    (b) heating the second stage reaction mixture to temperatures in the range of from about 98.9° to about 121.1° C.

7. The process of claim 6, wherein at least about 96% of the hydroxy groups of the sucrose are esterified by the end of said second stage with at least about 70% of the resulting sucrose esters being sucrose octaesters.

8. The process of claim 7 wherein said second stage is carried out under a pressure of at least about 30 mm Hg.

9. The process of claim 1 wherein the basic catalyst used during said second stage is an alkali metal alkoxide of a $C_1$–$C_4$ alcohol.

10. The process of claim 9 wherein the alkali metal alkoxide is selected from the group consisting of lithium methoxide, potassium t-butoxide, potassium methoxide, sodium methoxide, and mixtures thereof.

11. The process of claim 10 wherein the alkali metal alkoxide is potassium methoxide.

12. The process of claim 1 wherein said second stage reaction conditions further include one or more of the following reaction conditions:
    (c) keeping the molar ratio of fatty acid esters of the easily removable alcohol, to each esterifiable hydroxy group of the polyol in the second stage reaction mixture in the range of from about 0.9:1 to about 1.4:1;
    (d) removing materials having particle sizes greater than about 1 micron when the transesterification reaction reaches from about 50 to about 75% of completion;
    (e) when alkali metal alkoxides of $C_1$–$C_4$ alcohols are used as the basic catalyst, using the form of the catalyst that has been prepared and remains dissolved in the respective alcohol;
    (f) reducing the level of basic catalyst in the second stage reaction mixture to from about 0.01 to about 0.1 moles per mole of polyol;
    (g) adding from about 0.1 to about 1,000 moles, per mole of polyol, of a $C_1$–$C_4$ dialkyl carbonate to the second stage reaction mixture;
    (h) sparging the second stage reaction mixture with from about $1 \times 10^{-4}$ to about $1 \times 10^{-2}$ moles of carbon dioxide, per mole of polyol; or
    (i) adding from about 0.001 to about 10 moles, per mole of polyol, of a source of weakly acidic protons to the second stage reaction mixture.

13. The process of claim 12 wherein the molar ratio of fatty acid esters of the easily removable alcohol, to each esterifiable hydroxy group of the polyol in the second stage reaction mixture, is kept in the range of from about 0.9:1 to about 1.2:1.

14. The process of claim 12 wherein the basic catalyst used during said second stage is selected from the group consisting of lithium methoxide, potassium t-butoxide, potassium methoxide, sodium methoxide, and mixtures thereof, and wherein the level of catalyst is from about 0.02 to about 0.05 moles per mole of polyol.

15. The process of claim 12 wherein from about 0.1 to about 100 moles of dialkyl carbonate, per mole of polyol, is added to the second stage reaction mixture.

16. The process of claim 12 wherein the second stage reaction mixture is sparged with from about $4 \times 10^{-4}$ to about $4 \times 10^{-3}$ moles of carbon dioxide per mole of polyol.

17. The process of claim 12 wherein from about 0.01 to about 1 moles of weakly acidic protons, per mole of polyol, are added to the second stage reaction mixture and wherein the source of weakly acidic protons is selected from the group consisting of sucrose partial esters, solubilized sucrose, and alkali metal bicarbonates.

18. In a solvent-free, two-stage transesterification process for preparing highly esterified polyol fatty acid polyesters from a polyol and fatty acid esters of an easily removable alcohol, wherein said first stage comprises forming polyol fatty acid partial esters from a reaction mixture containing a polyol having at least 4 esterifiable hydroxy groups and the fatty acid esters of the easily removable alcohol in the presence of an effective amount of a basic catalyst and optionally an effective amount of soap emulsifier, and wherein said second stage comprises forming highly esterified polyol fatty acid polyesters from a reaction mixture containing the polyol fatty acid partial esters, fatty acid esters of the easily removable alcohol and an effective amount of a basic catalyst, the improvement which comprises carrying out said second stage under reaction conditions that provide a combined level of difatty ketones and β-ketoesters of about 300 ppm or less in the resulting highly esterified polyol fatty acid polyesters, and that result in at least about 96% of the hydroxy groups of the polyol being esterified, said reaction conditions including:

(a) controlling the level of easily removable alcohol in the liquid phase of the second stage reaction mixture to from about 10 to about 150 ppm; and (b) heating the second stage reaction mixture to temperatures in the range of from about 79.4° C. to about 135° C. and a pressure of at least about 30 mm Hg; and (c) sparging with an inert gas; and (d) keeping the molar ratio of fatty acid esters of easily removable alcohols to each esterifiable hydroxy group of the polyol in the range of from about 0.9:1 to about 1.4:1.

* * * * *